United States Patent [19]
Baker

[11] 3,952,741
[45] Apr. 27, 1976

[54] CONTROLLED RELEASE DELIVERY SYSTEM BY AN OSMOTIC BURSTING MECHANISM

[75] Inventor: Richard William Baker, Bend, Oreg.
[73] Assignee: Bend Research Inc., Bend, Oreg.
[22] Filed: Jan. 9, 1975
[21] Appl. No.: 539,637

[52] U.S. Cl. .............................. 128/260; 222/54; 222/491; 128/272
[51] Int. Cl.² ................... A61M 7/00; B65D 35/08
[58] Field of Search .............. 222/95, 92, 167, 153, 222/541, 54, 491; 424/19, 20; 128/260, 272

[56] References Cited
UNITED STATES PATENTS

| | | | |
|---|---|---|---|
| 3,247,066 | 4/1966 | Milosovich | 128/260 X |
| 3,710,795 | 1/1973 | Higuchi | 128/260 |
| 3,760,984 | 9/1973 | Theewes | 128/260 |
| 3,765,414 | 10/1973 | Arlen | 128/260 |
| 3,797,492 | 3/1974 | Place | 128/260 |
| 3,832,458 | 8/1974 | Merrill | 128/260 |
| 3,840,009 | 10/1974 | Michaels | 128/260 |

*Primary Examiner*—Aldrich F. Medbery

[57] ABSTRACT

An osmotic dispenser comprised of (1) a water permeable membrane forming part or all of the walls of an enclosure surrounding (2) an active agent, and in some cases (3) an additional compound known as an osmotic attractant which together exhibits an osmotic pressure against water. When placed in an aqueous environment water is osmotically drawn into the enclosure by the combined action of the agents (2) and (3) which distends and swells the enclosure until the membrane or some other part of the enclosure wall reaches the point of ultimate elongation and a portion of the wall yields and ruptures releasing the contents of the enclosure to the environment.

14 Claims, 10 Drawing Figures

FIG.1A  FIG.1B  FIG.1C
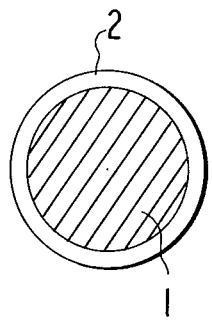
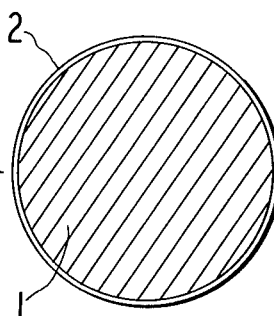
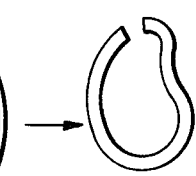
FIG.2
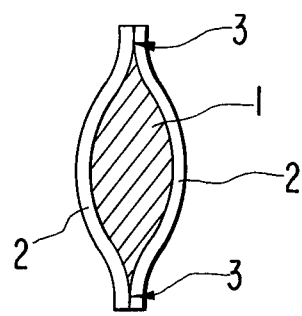
FIG.3
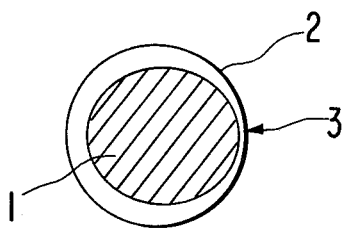

TOTAL DELIVERY RATE (SUM OF ALL DISPENSORS)

CONTROLLED RELEASE DELIVERY SYSTEM BY AN OSMOTIC BURSTING MECHANISM

BACKGROUND OF THE INVENTION

In the fields of medicine and agriculture it is often desirable to maintain an effective concentration of an active agent, for example a pesticide, herbicide, fertilizer or drug, at some site of action for a prolonged time. One method of achieving this goal is to deliver a large excess of the agent so that even though it is metabolized, excreted, or degraded, sufficient remains to maintain the effective dose. This approach is not only wasteful of the active agent but maintaining such a large excess during the early portion of the delivery period often leads to overdose-related side effects. A better pattern of delivery is to dispense the agent from a sustained release delivery system which releases the active agent at a slow rate throughout the delivery period. Many of these devices have been used and are described elsewhere, for example in "Controlled Release of Biologically Active Agents," A. C. Tanquary and R. E. Lacey (Eds) Plenum Press, New York, 1974 and the references therein. A plurality of the dispensers encompassed by this invention can also be used to deliver active agents at a more or less constant rate throughout the delivery period but in addition they can be programed to deliver the agents in periodic pulses at fixed time intervals or some other programed non-constant delivery regime. Many situations exist where periodic or non-constant delivery is desirable.

FIELD OF THE INVENTION

This invention relates to an osmotic dispenser, and, more especially, to an osmotic dispenser capable of releasing to its outside environment concentrations of active agent at an osmotically controlled rate over a prolonged period of time.

DEFINITION OF TERMS

The expression "active agent" as used herein denotes any drug (as defined, infra); composition in any way affecting any biological entity; substance having a nutrient or stimulating action, or growth inhibiting, destroying or any regulating action on plant growth, controlled or otherwise; substance to be assimilated by any organism, e.g., human being, animal, or lower order organism, for its nourishment or for regulating its growth; substance exhibiting any of the above activities to be directly applied to the habitat, surroundings or environment of any of the above organisms; and substance having any other effect on any other environment, especially any aqueous environment.

Therefore, suitable active agents for use with the dispenser of this invention include, without limitation, those which are generally capable of:

1. Preventing, alleviating, treating or curing abnormal and pathological conditions of the living body by such means as destroying a parasitic organism or limiting the effect of the disease or abnormality by chemically altering the physiology of the host or parasite;

2. Maintaining, increasing, decreasing, limiting or destroying a physiologic body or plant function, e.g., vitamin compositions, sex sterilants, fertility inhibitors, fertility promoters, growth promoters, herbicides, and the like;

3. Diagnosing a physiological condition or state;

4. Controlling or protecting an environment or living body by attracting, disabling, inhibiting, killing, modifying, repelling or retarding an animal or microorganism, such as food and non-food baits, attractants and lures, biocides, pesticides, algicides, parasiticides, rodenticides, insecticides, fungicides and the like;

5. Preserving, disinfecting or sterilizing; or

6. Controlling or affecting generically an environment, as by introducing a catalyst or metering a reactant into a reacting chemical system, or by effecting any chemical process therein, such as a fermentation, including propagation and/or attenuation or a microorganism.

The terms "environment," "surroundings" and "habitat" as used hereinabove and herein denote any prospective sites for the osmotic dispenser of this invention, or at least for the water permeable membrane component thereof, which is comprised of or will provide sufficient water for absorption into the device to develop the needed osmotic pressure on which its motive force depends; and implicit in the foregoing definition of "active agent" —one that will develop its action in the presence of such environment, surroundings or habitat, or one that will develop its action in a remote and/or another environment, which need not be aqueous, as hereinafter described and illustrated.

PRIOR ART

Many and varied compositions, products, appliances, depositors, applicators, dispensers, injectors, and devices are well known in the art in which timing or spacing of administration or absorption of an active agent is regulated by the structure or physical arrangement of elements so that a single administration provides a prolonged or sustained feeding of the active agent to a system by slow release. All such prior art devices and the like however are characterized by at least one feature which adversely affects control over their rate of release or which detracts from the practical benefits attendant to the long term administration of various active agents to humans, animals and into other environments.

Osmotic dispensers too have been proposed which are capable of delivery of active agents at a controlled rate. See Higuchi U.S. Pat. No. 3,760,805, Higuchi et al. U.S. Pat. Nos. 3,732,865, and 3,760,804 and Theeuwes U.S. Pat. No. 3,760,984. In essence these devices consist of two chambers separated by a piston or flexible membrane. One chamber containing the active agent is surrounded by an impermeable wall pierced by an orifice. The second chamber containing an osmotic agent is separated from the outside environment by a semi-permeable membrane. The osmotic agent draws water into its chamber which then produces a hydraulic pressure on the piston or flexible membrane separating this chamber from the active agent-containing chamber. Thus as water is progressively imbibed by one chamber an equal volume of active agent is expelled from the second chamber. These devices, however, have substantial inherent disadvantages which have prevented their wide acceptance. In the first place, the active agent has to be dispensed as a solution or a fine dispersion suspended in some form of carrier medium. The active agent is therefore in contact with or dissolved in a liquid environment during the entire shelf storage period. Many agents have limited stability in these environments and will degrade before use. Secondly the maximum agent loading that it is possible to achieve with most of these devices is usually of the order 50 vol.%. Thirdly, the construction of even the simplest of these devices, for example that of Theeuwes U.S. Pat. No. 3,760,984, is still costly and complicated. Finally, these osmotic dispensers are programed to deliver active agents at an approximately constant rate. In many situations this is desirable but in others periodic high doses of agent followed by little or no delivery of the active agent or some other non-constant delivery regime is required. This type of delivery regime is not attainable with the above described devices.

A second type of controlled dispensing device is described by Milosovich in U.S. Pat. No. 3,247,066. This patent discloses a core comprising a mixture of drug and a water-swellable colloid coated with a water permeable polymer. When taken by mouth, water in the body fluids permeates the outer coating causing the colloid to hydrate and to swell and break the outer coating thus releasing the drug. Among the suitable colloids described are gelatin, starch, zein, agar, etc. This device also suffers several inherent defects. Thus, the swelling of colloids is greatly influenced by the pH of the environment of the colloid and the presence of other components in both the external and internal environments of the device. Thus with many drugs the colloids swell little or not at all. Secondly, most colloids consist of molecules with a range of molecular weights and chemical compositions and their swelling behavior can vary substantially from source to source and even lot to lot making the construction of reliable devices difficult. Thirdly, the loading of active agent possible with this type of device is limited since a large volume of the device must be filled with the colloid to burst the enclosure since the swelling that colloids undergo on hydration is usually limited. Finally, the degree of variability and control of the time of bursting afforded by colloids with their limited swelling on hydration is not large.

SUMMARY OF THE INVENTION

Accordingly, it is an object of this invention to provide the benefits of long term administration of an active agent both to animals, humans, and into other environments. Another object of this invention is to provide an improved osmotic dispenser which overcomes problems inherent in related devices heretofore proposed.

Another object of this invention is to provide an improved osmotic dispenser which will permit high concentrations of an active agent to be embodied therein and in which such high concentrations of active agent will neither exhibit the tendency to be leached from the device nor to be decreased in potency by chemical breakdown.

Another object of this invention is to provide an osmotic active agent dispenser which depends for its release of active agent on the design of the device and agents incorporated in the device and is independent of the environment of use.

Another object of the invention is to provide an osmotic dispenser of simple design which will release the active agent at a controlled rate over a prolonged period of time.

Yet another object of this invention is to provide an osmotic dispenser of simple design so that a plurality of said dispensers can release the active agent as a single pulse or as several discrete pulses.

In attaining the object of this invention an active agent capable of developing an osmotic pressure is incorporated within an enclosure, part or all of which is formed from a semi-permeable membrane which is impermeable to the active agent but is permeable to water. When placed in an aqueous environment, or in an environment with a relative humidity in excess of the active agent's saturated solution relative humidity, water is imbibed because of the difference in osmotic pressure across the membrane. As this water is imbibed it produces an hydraulic pressure inside the enclosure which distends the walls of the enclosure. This process continues until at some point a portion of the enclosure's walls reaches its point of maximum elongation and the container wall breaks and the contents of the container are released to the environment. The time delay between the time the device is placed in the aqueous environment and the time when it bursts can be controlled by (i) varying the thickness or area or material of composition of the semi-permeable membrane to increase or decrease the rate of permeation of water into the enclosure. (ii) To increase or decrease the thickness or material of composition or shape of part of the enclosure to alter the strength of the enclosure and alter the volume of water which must be imbibed before the enclosure bursts. (iii) By encapsulating an osmotic additive in addition to the active agent into the enclosure which can supplement the osmotic pressure of active agent thus speeding the imbibition of water. By this last expedient, devices can be made with active agents which have only low osmotic pressures. Other objects, features, and advantages of this invention will be apparent from the following description when taken in conjunction with the accompanying drawings and examples.

BRIEF DESCRIPTION OF THE DRAWINGS

FIG. 1 is a cross section of an osmotic dispenser in the form of a tablet illustrating the mechanism by means of which the dispenser is believed to operate.

FIG. 1(A) is a cross section of the osmotic dispenser before placement in the aqueous environment.

FIG. 1(B) is a cross section of the osmotic dispenser after some time in the aqueous environment.

FIG. 1(C) is a cross section of the osmotic dispenser after a portion of the dispenser wall has ruptured.

FIG. 2 is a cross sectional view of an osmotic dispenser incorporating a seam. This dispenser ruptures along this seam.

FIG. 3 is a cross sectional view of a dispenser following this invention where a weak spot is produced by making a thin spot in the semipermeable membrane.

FIG. 6 shows several schematic delivery-time curves that can be obtained with a plurality of the dispensers covered by this invention.

DETAILED DESCRIPTION OF THE INVENTION

Figure 4:
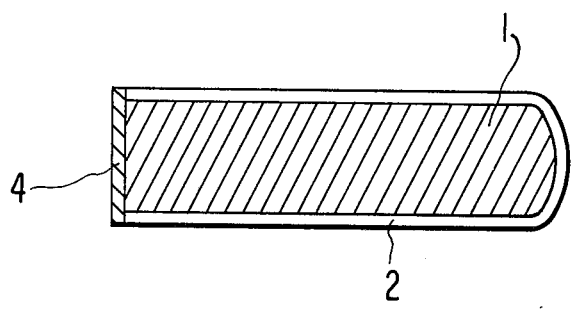
FIG. 4 illustrates a dispenser following this invention in which a weak spot is formed by forming part of the walls of the dispenser from a material with a low yield strength.

The Membrane: The driving force for the mechanism of action of this dispenser is provided by osmotic imbibition of water through a semipermeable membrane causing a swelling or distortion of the enclosure until at some time a portion of the enclosure wall reaches its maximum elongation and breaks. The contents of the dispenser are then released to the environment. A principal factor controlling the rate of imbibition of water into the dispenser is the thickness and water permeability of the membrane and by choice of the membrane material the time to release of the active agent can be easily varied by as much as 1000-fold. Water permeability data which can be used to guide the selection of an appropriate membrane material can be found in articles by M. Salame, Journal of Polymer Science, Polymer Symposia Series No. 41, p. 1–15 (1973), and by J. Barrie in "Diffusion in Polymers," J. Crank and G. S. Park (Eds), Academic Press, London (1968), and by tables in "The Guide to Plastics," Modern Plastics Encyclopedia, McGraw Hill, New York (19700265). Amongst the preferred polymers with high water permeabilities are cellulose acetate, cellulose acetate butyrate, cellulose nitrate, crosslinked polyvinyl, alcohol, polyurethanes, nylon 6, nylon 6.6, and aromatic nylon such as Nomex manufactured by DuPont. Preferred polymers with intermediate permeabilities include polyvinyl acetate, plasticized polyvinyl acetate, polyvinyl butyrate, and ethylene vinyl acetate co-polymers. Preferred polymers with low water permeabilities include polyethylene, polypropylene, polyisobutylene, polyvinyl chloride, plasticized polyvinyl chloride, natural rubber, silicone rubber and polybutadiene.

In general large changes in the time to release of the active agent from the dispenser are most economically and easily achieved by varying the membrane material while small changes of up to a factor of five are best achieved by varying the thickness of the membrane. In general a membrane thickness of at least one thousanth of an inch (mil.) is required to obtain sufficient mechanical strength for handling of the dispenser. However, with small dispensers such as microcapsules lesser thicknesses are satisfactory. The membrane should be stable both to the outside environment and in the presence of a saturated solution of the contents of the dispenser. The membrane should also be relatively impermeable to the contents of the dispenser so that active agent or osmotic attractant is not lost by diffusion from the dispenser prior to rupture and so that a large osmotic pressure is obtained. This condition is met if the water flux into the dispenser is of the order of 5 or more and preferably 10 or more times greater than the loss of the active agent or osmotic agent from the dispenser.

The Extention to Break: When placed in an osmotic environment, water is imbibed by the dispenser. At first the water fills any void space within the dispenser after which it will distend the dispenser until at some point the dispenser breaks and releases the active agent. This sequence is shown in FIG. (1) where (1) represents the active agent together with any osmotic attractant present and (2) represents the semipermeable membrane. FIG. (1-A) shows the initial state of the dispenser. When placed in an aqueous environment it slowly swells to the shape shown in FIG. (1-B) and then as the ultimate elongation of the wall material is reached the wall breaks and releases the active agent as shown in FIG. (1-C).

One method of controlling the time at which release of the active agent takes place is to vary the ultimate elongation of the material from which the enclosure walls are made. One method of obtaining the ultimate elongation of a material is to clamp a small piece between the jaws of an Instron testing machine and pull the jaws slowly apart at a rate of less than 0.1 cm/min until the point of ultimate elongation is reached. The ratio of the initial length to the final length can then be used to estimate how much water will be imbibed by the device before it breaks. In some cases (for example, for reasons of biological compatability) it may be desirable to make the semipermeable membrane from a material which has an unsuitably high elongation to break. In this case weak spots can be placed in the structure of the dispenser which will rupture before the rest of the membrane material approaches its ultimate elongation. Thus in FIG. 2 the dispenser is made by sealing two flat sheets of the semi-permeable membrane material 2 around a core 1 of the active agent (and osmotic attractant if present). The seal of this dispenser 6 can be made to rupture well before the membrane reaches its ultimate elongation. Moreover, by altering the pressure and temperature used by a heat sealer or the glue used in a solvent seal the time of rupture can be controlled over wide limits.

FIG. 3 illustrates another form of weak spot 3 that can be incorporated into the dispenser, i.e., by making the membrane wall 2 thinner at some point. When placed in an aqueous environment the capsule will break preferentially at this point.

A third method of altering the time of rupture is illustrated in FIG. 4 which shows a semipermeable membrane 2 in the form of a cylinder filled with an active agent (and osmotic attractant if present) 1. The device is sealed at one end with a second material 4. In this example the material 4 is made from a weaker material than the membrane material. For example the cylinder could be made from cellulose acetate and the cap from ethylene vinyl acetate. Cellulose acetate is fairly tough and strong, while ethylene vinyl acetate is relatively weak and rubbery; thus, when placed in an aqueous environment water is imbibed through the cellulose acetate semipermeable membrane. This water distorts both the cellulose acetate tube and the ethylene vinyl acetate end cap but because the ethylene vinyl acetate is much more rubbery and weaker it distorts more and finally ruptures well before the yield point of the cellulose acetate is reached.

Figure 5:
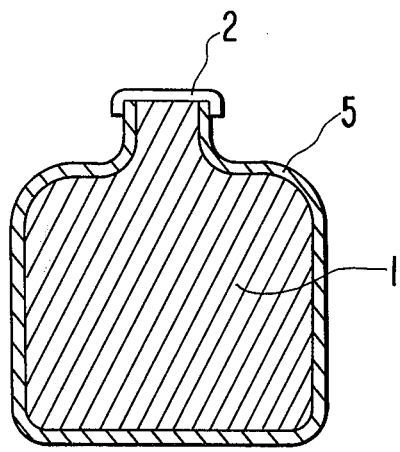
FIG. 5 illustrates a device following this invention in which only part of the dispenser walls consists of a semipermeable membrane.

A fourth type of device is illustrated in FIG. 5 which shows a container 5 made from an essentially impermeable material but which has a portion of the container walls made from a semipermeable membrane material 2. As before the active agent (and osmotic attractant if present) cause water to be imbibed through the semipermeable membrane until at some time the container ruptures releasing the agent to the environment. By altering the ratio of the area of the impermeable wall to the membrane, the time to rupture can be altered.

The Osmotic Pressure: If a semipermeable membrane separates a solution from pure water or two solutions of different concentrations the tendency to equalize concentrations will result in a flow of water from the less concentrated solution to the other one. If an attempt is made to impede this flow by exerting a pressure on the solution (assuming for simplicity the other phase is pure solvent) the rate of flow will be decreased. As the pressure is increased a point will be found when the flow is brought to a complete stop. This equilibrium pressure is called the osmotic pressure. Osmotic pressures can be calculated in a variety of ways as for example those given by C. E. Reid in "Desalination by Reverse Osmosis," M. Merten (Ed), MIT Press, Cambridge, Mass. (1966). The simplest approximate method due to Van't Hoff has the form $$\pi = CRT$$

where $\pi$ is the osmotic pressure of the solution, $C$ is the molar concentration of the solute in the solution, $R$ is the gas constant and $T$ is the absolute temperature. A few trial calculations show that osmotic pressures of saturated solutions of even moderately soluble compounds are very high and of the order of several hundreds and even thousands of pounds per square inch. Typical values for saturated solutions are for example NaCl (26.5W% solubility) $\pi = 5,300$ psi, $(NH_4)_2 SO_4$ (43.2W% solubility) $\pi = 4,100$ psi. The pressure required to distort and rupture the walls of the enclosures described in this invention is relatively small in comparison and thus the pressures that build up inside the enclosure prior to rupture usually do not inhibit the influx of water into the device. If, however, the enclosure walls must be thick for reasons of physical integrity, for example, or if the active agent has only a low solubility and hence osmotic pressure, or if the solution outside of the enclosure has a high osmotic pressure, the pressure that builds up inside the container may approach and even fall below the pressure required to burst the enclosure. In this case the performance of the device may be erratic and it may even not release the active agent at all. It then becomes desirable to supplement the osmotic pressure due to the active agent by incorporating a second compound called an osmotic attractant with the active agent into the enclosure. The osmotic attractant is drawn from those compounds which have relatively high osmotic pressures, do not degrade or interfere with the membrane or the enclosure walls, and do not interfere with the action of the active agent or the environment into which it is ultimately released. Typical but non-limiting examples are sodium chloride, magnesium chloride, magnesium sulphate, potassium sulphate, sodium sulphite, sodium sulphate, sodium acetate, ammomium phosphate, ammonium sulphate, sucrose, glucose, raffinose, calcium lactate, and magnesium succinate. A measure of control of the time to release of the active agent is possible by choice of the amount and the osmotic pressure of the osmotic attractant added. The total osmotic pressure of the contents of the dispenser must exceed the pressure required to distort the dispenser both initially and just prior to rupture when the water imbibed will have diluted the system. The most reliable and reproducible operation is obtained if the amount of swelling of the dispenser and the solubility of the active agent (and osmotic attractant if present) are matched so that some excess agent remains just prior to rupture. In this way, the osmotic pressure of the internal environment (which draws water into the dispenser) is constant throughout the dispenser lifetime. In some cases this is not possible; for example, with very soluble active agents, the dispenser will still swell and rupture but the ability to reproduce the same time to rupture for similar devices may be somewhat impaired.

Fabrication of the Invention: The osmotic dispenser can be fabricated in any convenient shape for either physical insertion or implantation in the body, or for administration via the gastrointestinal tract, or for incorporation into a sprayable formulation, or for incorporation into a formulation which can be broadcast onto fields and waterways or for introduction into any desired environment. Dimensions of the device can thus vary widely and are not of controlling importance. The lower limit of the size of the device is governed by the amount of the particular active agent to be supplied to the environment to elicit the desired response as well as by the form the dosage unit takes, for example in cases of specific body uses, implantate, bolus, IUD, IVD, vaginal ring, uterine capsule for fertililty suppression, pessary, suppository and the like. This holds, too, with respect to the upper limit on the size of the device. In the above paragraph the device is used in its broad sense and may include a plurality of osmotic dispensers combined in some way to form a single larger device. Thus when the dosage form includes a plurality of dispensers having individual variations with respect to the rate of agent release i.e., a plural dosage form there is provided on administration a controlled release dosage form. In this condition, each dispenser becomes separately ruptured in due course depending on the film coating, thickness, composition, contents, etc. of each individual dispenser. In controlled fashion some dispensers rupture first to provide prompt release of agent, others later to provide a sustained effect.

Several of the methods of making the osmotic dispensers described above are given here by way of example. Variations and other manufacturing techniques will be obvious to those skilled in the art. For large dispensers, injection molding can be used. In general the sequence used will consist of making the major portions of the enclosure in one molding cycle. The active agent and osmotic attractant if present is then placed in the enclosure and the enclosure sealed in a second injection molding cycle. The principal difficulties with injection molding are that it is difficult to economically and reproducibly make the membrane portion or any other portion of the enclosure less than 3 to 4 mils. thick, the internal volume of the enclosure should normally be at least 0.5 cm$^3$ in volume, the initial cost of the injection mold is high (although this can be depreciated over a very large number of capsules) and injection molding is not possible with all polymers. On the other hand, with injection molding it is easy to make enclosures with built-in weak spots, to make large devices and to make devices in large numbers very reproducibly. For small dispensers with internal volumes of 0.1 cm$^3$ to 5 cm$^3$ conventional tableting and coating as used in the Pharmaceutical industry and described in "The Theory and Practice of Industrial Pharmacy" by L. Lachman, H. A. Lieberman, and J. L. Kanig (Eds), Lea and Febiger (Pub), Philadelphia (1970) or Remington's Pharmaceutical Sciences, A. Osol et al. (Eds.) Mack Publishing Co., Easton, Pa. (1970) are preferred. In general with this equipment the membrane must form the entire wall of the enclosure but the process is very cheap and economical.

An alternate method, with moderate sized devices with volumes of active agent 0.1 cm$^3$ and up, is to use pipes or tubes packed with active agent sealed at both ends. Alternatively, the device can be made by laminating the active agent between two sheets of film. These last two methods are particularly suited to the economical fabrication of small numbers of dispensers for limited laboratory, field, or clinical trials. If the amount of the active agent to be delivered is small it can be diluted with an inert ingredient (chalk, saw dust, etc.) or osmotic attractant and used with one of the devices described above or it can be made in the form of microcapsules. Many forms of production of microcapsules are possible and are described in reviews by J. A. Herbig in "The Encyclopedia of Polymer Science and Technology," Interscience Publishers 8, 719, (1968) and H. Nack, "Journal of the Society of Cosmetic Chemists" 21, 85, (1970) and the references therein.

Figure 6A:
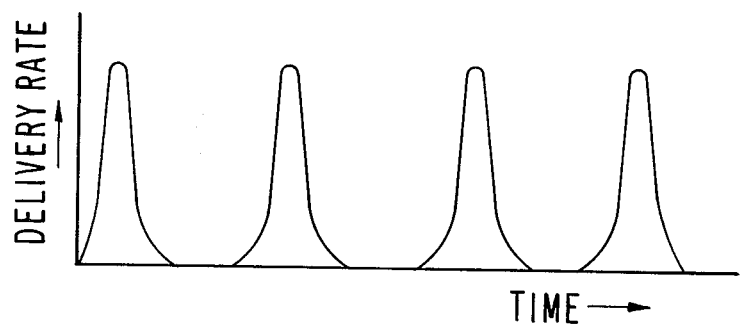
FIG. 6(A) is a plot showing the pulsating pattern of release attainable by a plurality of osmotic dispensers designed to release at widely separate times.
Figure 6B:
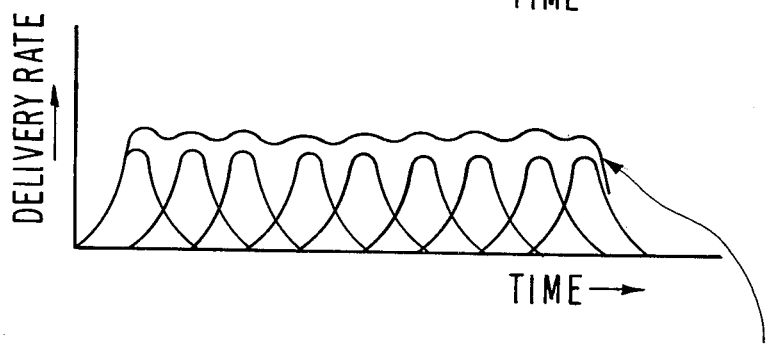
FIG. 6(B) is a plot showing the almost constant pattern of release attainable by a plurality of dispensers designed to release in close sequence.
Figure 6C:
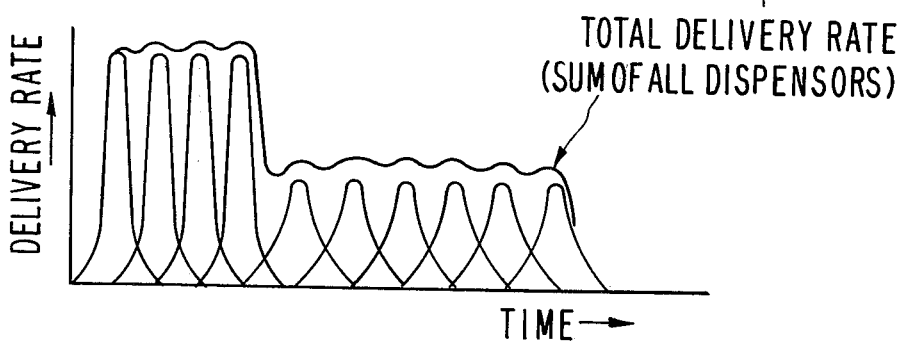
FIG. 6(C) is a plot showing the delivery pattern attainable by a mixture of a plurality of two types of osmotic dispenser, several large dispensers designed to release during an initial period and several smaller ones designed to release sequentially at a later time.

Active Agent Release From the Invention: The invention described herein has many unique features hitherto unattainable by other means. One of these features is the ability to release a known amount of the agent after a known residence time of the dispenser in the environment. This feature allows almost any pattern of delivery of active agent to be obtained by making plural dosage forms consisting of several dispensers placed in the same environment at the same time; each dispenser or subgroup of dispensers being made slightly different so that it releases its agent at a different time. By this mechanism the pattern of release of the active agent can be varied over a wide range. FIG. 6 shows by way of example some of the patterns attainable. FIG. 6-A might be the release pattern desirable with an aquatic herbicide, for example, where delivery of the agent is required as a large dose every 3 to 6 months; FIG. 6-B might be the pattern of release desired for drugs such as lithium chloride, potassium chloride or saliciyic acid and its derivitives which are known to produce undesirable side effects if given orally in a single readily available form. In this case the delivery would be spread over a period of 8 to 12 hours. FIG. 6-B might also represent the release of a pesticide, for example, parathion (which because of its low solubility would be admixed with an osmotic attractant). Parathion is a potent pesticide but in soil it is metabolized rapidly by microorganisms and thus does not last through the growing season when given as a conventional dose. Administration at a slow constant rate over a 3 to 4 month period as shown in FIG. 6-B is thus desirable. FIG. 6-C might represent the pattern of release desirable with antibiotic drugs such as tetracycline where a large initial "loading" dose is desired followed by a lower, more or less constant, holding dose. This type of dosage form is useful in cattle feed additives in the prevention of shipping fever where delivery of the drug over a 3 to 5 day period is required.

While the invention has been described and illustrated with reference to certain preferred embodiments, those skilled in the art will appreciate that various modifications, changes, substitutions, and omissions can be made without departing from the spirit of the invention. It is intended therefore that the invention be limited only by the scope of the following claims.

What is claimed is:

1. A water actuated osmatic type active agent dispenser including a means for dispensing a dosage of active agent into an aqueous fluid or humid environment comprising (1) a fluid permable membrane defining at least a part of a walled enclosure, said enclosure containing therein an active agent which exhibits an osmatic pressure upon exposure of the enclosure to the environment, the thickness and permibility of said membrane comprising a means for controlling the water diffusion therethrough until the osmotic pressure in the enclosure is sufficient to distort, stretch and finally rupture the enclosure resulting in release of the agent to the environment.

2. An osmotic dosage form comprising a plurality of dispensers as set forth in claim 1 wherein said membrane and agent combination is related in a progressive series over a predetermined range such that on prolonged exposure to said aqueous or humid environment the diffusion of water takes place at related varying rates causing the serial bursting of the individual dispensers.

3. An osmotic dispenser as set forth in claim 1 wherein at least a part of the agent is an herbicide.

4. An osmotic dispenser as set forth in claim 1 wherein at least a part of the agent is a pesticide, insecticide or larvicide.

5. An osmotic dispenser as set forth in claim 1 wherein at least a part of the agent is a fertilizer.

6. An osmotic dispenser as set forth in claim 1 wherein at least a part of the agent is an animal or human medicament.

7. An osmotic dosage form as set forth in claim 1 wherein at least a part of the agent is a medicament and the aqueous environment is the gastrointestinal fluid.

8. An osmotic dispenser as set forth in claim 1 wherein a portion of the agent (2) is a biologically or chemically active material and a portion of the agent is an osmotic attractant by means of which the rate of water diffusion into the enclosure and hence subsequent rupture of the enclosure can be regulated.

9. An osmotic dosage form comprising a plurality of dispensers as set forth in claim 8 wherein the membrane, or the osmotic attractant or a combination of these is related in a progressive series over a predetermined range such that on prolonged exposure to an aqueous or humid environment the diffusion of water takes place at related varying rates causing the serial bursting of the individual dispensers.

10. An osmotic dispenser as set forth in claim 8 wherein the biologically active agent is an herbicide.

11. An osmotic dispenser as set forth in claim 8 wherein the biologically active agent is a pesticide, insecticide or larvicide.

12. An osmotic dispenser as set forth in claim 8 wherein the biologically active agent is a fertilizer.

13. An osmotic dispenser as set forth in claim 8 wherein the biologically active agent is an animal or human medicament.

14. An osmotic dispenser as set forth in claim 1 wherein the enclosure wall contains a weak spot or seam which on exposure of the dispenser to the aqueous or humid environment and subsequent imbibition of water causes the enclosure wall to rupture at the weak spot or seam resulting in release of the agent to the environment at a time determined by the strength of the weak spot or seam.

* * * * *

REEXAMINATION CERTIFICATE (43rd)

United States Patent [19]
Baker

[11] B1 3,952,741
[45] Certificate Issued  Jan. 18, 1983

[54] CONTROLLED RELEASE DELIVERY SYSTEM BY AN OSMOTIC BURSTING MECHANISM

[75] Inventor: Richard William Baker, Bend, Oreg.

[73] Assignee: ALZA Corp., Palo Alto, Calif.

Reexamination Request
No. 90/000,085, Oct. 14, 1981

Reexamination Certificate for:
Patent No.: 3,952,741
Issued: Apr. 27, 1976
Appl. No. 539,637
Filed: Jan. 9, 1975

[51] Int. Cl.³ .................... A61M 7/00; B65D 35/08
[52] U.S. Cl. .......... 128/260; 222/54; 222/491; 128/272
[58] Field of Search .................................. 128/260, 261

[56] References Cited

U.S. PATENT DOCUMENTS

| | | | |
|---|---|---|---|
| 3,247,066 | 4/1966 | Milosovich | 128/260 |
| 3,710,795 | 1/1973 | Higuchi | 128/260 |
| 3,760,984 | 9/1973 | Theeuwes | 128/260 |
| 3,765,414 | 10/1973 | Arlen | 128/260 |
| 3,797,492 | 3/1974 | Place | 128/260 |
| 3,832,458 | 8/1974 | Merrill | 128/260 |
| 3,840,009 | 10/1974 | Michaels | 128/260 |
| 3,916,899 | 12/1975 | Theeuwes | |
| 3,923,939 | 12/1975 | Baker | |
| 4,177,256 | 12/1979 | Michaels | |

FOREIGN PATENT DOCUMENTS

| | | |
|---|---|---|
| 742639 | 1974 | South Africa. |
| 1093286 | 11/1967 | United Kingdom. |

*Primary Examiner*—C. Fred Rosenbaum

[57] ABSTRACT

An osmotic dispenser comprised of (1) a water permeable membrane forming part or all of the walls of an enclosure surrounding (2) an active agent, and in some cases (3) an additional compound known as an osmotic attractant which together exhibits an osmotic pressure against water. When placed in an aqueous environment water is osmotically drawn into the enclosure by the combined action of the agents (2) and (3) which distends and swells the enclosure until the membrane or some other part of the enclosure wall reaches the point of ultimate elongation and a portion of the wall yields and ruptures releasing the contents of the enclosure to the environment.

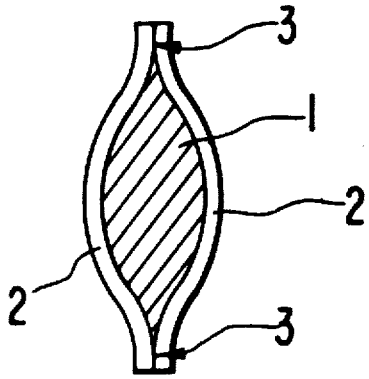

ature enclosed in heavy brackets appeared in the
REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent, matter printed in italics indicates additions made to the patent.

AS A RESULT OF REEXAMINATION, IT HAS BEEN DETERMINED THAT:

Claims 1–14, having been determined to be unpatentable, are cancelled.

New claims 15–22 are added and determined to be patentable.

*15. An osmotic dosage form comprising, in combination, a plurality of individual discreet dispensers for dispensing a predetermined amount of active agent into an aqueous fluid or a humid environment, each such dispenser comprising:*

*(a) a wall member defining a hollow enclosure having an enclosed volume sized to receive said predetermined amount of active agent; said wall member having a semipermeable portion and an impermeable portion, said semipermeable portion being permeable to the flow of water through said wall while being substantially impermeable to the flow of water and the flow of active agent, and*

*(b) an active agent within said hollow enclosure, said active agency exhibiting an osmotic pressure on exposure of said dispensers to the environment sufficient to distort, stretch and finally rupture said wall member resulting in the immediate release of the agent to the environment;*

*the relationship between the surface area of said permeable and impermeable portions of said wall member varying within the population comprising the plurality of dispensers whereby a predetermined and sequential bursting of individual dispensers releases the active agent from said dosage form in a predetermined manner over a prolonged period of time.*

*16. An osmotic dosage form as set forth in claim 15 wherein at least a part of the agent is an herbicide.*

*17. An osmotic dosage form as set forth in claim 15 wherein at least a part of the agent is selected from the group consisting of a pesticide, and insecticide and a larvacide.*

*18. An osmotic dosage form as set forth in claim 15 wherein at least a part of the agent is a fertilizer.*

*19. An osmotic dosage form as set forth in claim 15 wherein at least a part of the agent is an animal or human medicament.*

*20. An osmotic dosage form as set forth in claim 15 wherein at least a part of the agent is a medicament and the aqueous environment is the gastrointestinal fluid.*

*21. An osmotic dosage form as set forth in claim 15 wherein a portion of the agent is a biologically or chemically active material and a portion of the agent is an osmotic attractant by means of which the rate of water diffusion into said enclosure and hence subsequent rupture of the enclosure can be regulated.*

*22. An osmotic dosage form as set forth in claim 15 wherein the enclosure wall contains a weak spot or seam which on exposure of the dispenser having such weak spot or seam to the aqueous or humid environment and subsequent imbibition of water causes the enclosure wall to rupture at said weak spot or seam resulting in release of agent to the environment at a time determined by the strength of the weak spot or seam.*

* * * * *